United States Patent [19]

Grate et al.

[11] Patent Number: 4,687,872

[45] Date of Patent: Aug. 18, 1987

[54] PROCESS FOR THE PREPARATION OF URETHANES

[75] Inventors: John H. Grate; David R. Hamm, both of Mountain View, Calif.

[73] Assignees: Catalytica Associates, Mountain View, Calif.; Haldor Topsoe A/S, Copenhagen, Denmark

[21] Appl. No.: 806,389

[22] Filed: Dec. 9, 1985

[51] Int. Cl.[4] ............... C07C 125/065; C07C 125/073
[52] U.S. Cl. .................................. 560/25; 560/24; 560/26; 560/27; 560/28; 560/29; 560/30; 560/31; 560/32; 560/33; 560/115; 560/157; 560/158; 560/160; 560/163; 560/165
[58] Field of Search ............... 560/24, 25, 26, 27, 560/29, 30, 31, 32, 33, 28, 115, 157, 158, 166, 163, 160, 165

[56] References Cited

U.S. PATENT DOCUMENTS

| | | | |
|---|---|---|---|
| 3,338,956 | 8/1967 | Mountfield | 560/24 |
| 3,993,685 | 11/1976 | Zajacek et al. | 560/24 X |
| 4,052,437 | 10/1977 | Licke | 560/24 X |
| 4,491,670 | 1/1985 | Bhaduri et al. | 560/24 |

FOREIGN PATENT DOCUMENTS 2555557  6/1976  Fed. Rep. of Germany ........ 560/24

*Primary Examiner*—Michael L. Shippen
*Attorney, Agent, or Firm*—John H. Grate; Robert J. Baran

[57] ABSTRACT

A process for preparing urethanes by reacting a solution of a nitrogen-containing organic compound and a hydroxyl-containing organic compound with carbon monoxide in the presence of a catalyst comprising rhodium, as a metal or compound, is disclosed. In the process of this invention, the rate of conversion and selectivity to urethane is increased by providing a rhodium catalyst comprising a polyamino ligand having at least two tertiary amino groups capable of coordinating with rhodium.

24 Claims, No Drawings

PROCESS FOR THE PREPARATION OF URETHANES

BACKGROUND OF THE INVENTION

1. Field of the Invention

This invention relates to a process for preparing urethanes by reacting a solution of a nitrogen-containing organic compound and a hydroxyl-containing organic compound with carbon monoxide in the presence of a rhodium catalyst.

2. Description of the Art

Various patents have disclosed methods for carbonylating nitrogen-containing organic compounds—e.g., nitro compounds, amines, azo- and azoxy compounds,—to urethanes in the presence of a platinum group metal-containing catalyst usually a palladium or rhodium-containing catalyst and most often a palladium or rhodium halide-containing catalyst. Generally, a co-catalyst (promoter) has been needed in combination with the platinum group metal-containing catalyst in order to obtain improved rates of reaction. The vast majority of prior art processes use, as a co-catalyst, a halide salt of a metal which is redox-active under the reaction conditions, usually iron, and most often iron chlorides. The co-catalyst is used in substantial molar excess compared to the main catalyst in order to obtain the desired reaction rate. These large quantities of redox-active metal halides are troublesome to separate from the reaction product and cause substantial corrosion problems.

A few references have taught the addition of a primary amino compound (and/or related compounds, such as urea, biurets, and allophanates) to further improve the rate and selectivity of reactions catalyzed by a platinum group metal compound in combination with a redox-active metal halide-cocatalyst. U.S. Pat. No. 4,178,455 discloses that, in a process for converting nitroaromatic to urethane catalyzed by a platinum, palladium, rhodium, or ruthenium compound and a Lewis-acid promoter, the rate and selectivity are improved by adding to the reaction, an organic primary amino compound, a urea compound, a biuret compound, an allophanate compound, or a mixture thereof. The preferred Lewis acid promoters are redox-active metal salts, especially iron chlorides. This patent illustrates (by example) only palladium catalysts with iron chloride promoters. A careful study of the examples reveals that the starting nitroaromatic and the primary amino compound (or related compound) are both converted, in net, to urethane. Thus, when the primary amino compound or urea compound contains the same aryl group as the starting nitroaromatic compound the reported yield of urethane, based on only the nitroaromatic converted, exceeds 100%. This patent also teaches the use of tertiary amines, e.g. pyridine, in large molar excess compared to the palladium catalyst to prevent corrosion. See also U.S. Pat. No. 4,186,269 wherein a tertiary amine, e.g. pyridine, in large molar excess is utilized to suppress corrosion in a process utilizing a catalyst system comprising (1) palladium, ruthenium, rhodium or compounds thereof, and (2) a Lewis Acid, e.g. ferric chloride. Similarly, U.S. Pat. Nos. 4,219,661; 4,262,130; and 4,339,592 teach palladium catalysts with iron oxide and iron chloride co-catalysts in which addition of tertiary amines is one embodiment. Pyridine is the demonstrated tertiary amine used in large molar excess relative to palladium and the stated purpose of the pyridine is to decrease undesirable secondary reactions of the alcohol reactant. No effect of the tertiary amines on the activity of the catalyst towards urethane synthesis is disclosed.

U.S. Pat. No. 4,297,501 discloses a process in which mixtures of a primary amine and a nitroaromatic are carbonylated to urethane with a Group VIII noble metal compound and an oxychloride compound capable of undergoing redox reactions. Alternatively, an oxide compound capable of undergoing redox reactions in combination with an anionic chloride compound is used as the promoter system. Illustrated, by example, are $PdCl_2$ and $RhCl_3$, as Group VIII noble metal compounds, and the oxides and chlorides of vanadium and iron. In the preferred embodiment of U.S. Pat. No. 4,297,501, the nitroaromatic corresponds to the primary amine, and the patent teaches the following reaction stoichiometry:

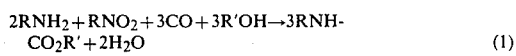

$$2RNH_2 + RNO_2 + 3CO + 3R'OH \rightarrow 3RNHCO_2R' + 2H_2O \quad (1)$$

U.S. Pat. No. 4,297,501 further teaches that when nitroaromatic is present in excess of the 1:2 ratio relative to amine, the remaining nitroaromatic is converted to urethane by the following reaction stoichiometry:

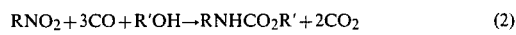

$$RNO_2 + 3CO + R'OH \rightarrow RNHCO_2R' + 2CO_2 \quad (2)$$

It can be seen from the above equations that when primary amine is initially present, in processes which convert nitroaromatic to urethane using Group VIII noble metals in combination with redox-active metal halide co-catalysts, the primary amine is, in net, consumed to also make urethane. (See equation (1) above). Once the primary amine is consumed to low levels, any remaining nitrobenzene is converted to urethane via reaction equation (2) above. Since the primary amine is already consumed to low levels, it is no longer available to favorably influence the rate of the process according to said reaction (2).

This patent does not teach the addition of a tertiary amine to the disclosed catalyst and promoter.

U.S. Pat. No. 4,304,922 similarly discloses a process in which mixtures of N,N'-diaryl urea and nitroaromatic are carbonylated to urethane with the same catalyst/co-catalyst systems of U.S. Pat. No. 4,297,501. Illustrated by examples are $PdCl_2$, $RhCl_3$, $IrCl_3$, $PtCl_4$ and $RuCl_3$ as Group VIII noble metal compounds. Iron oxychloride and several other redox active metal oxides and chlorides are illustrated as co-catalysts. In examples in which redox active metal oxides are used, anilinium hydrochloride is also added to provide active anionic chloride. In the preferred embodiment of this patent, the N,N'-diaryl urea and nitroaromatic have the same aryl groups, and the patent teaches that the following reaction stoichiometry is obtained:

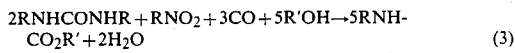

$$2RNHCONHR + RNO_2 + 3CO + 5R'OH \rightarrow 5RNHCO_2R' + 2H_2O \quad (3)$$

It is known that N,N' diarylureas react with alcohols to produce urethane plus amine; see for Example U.S. Pat. No. 2,409,712, wherein the following reaction is disclosed:

$$RNHCONHR + R'OH \rightarrow RNHCO_2R' + RNH_2 \quad (4)$$

It can be seen that once this occurs under the reaction conditions, the same process as U.S. Pat. No. 4,297,501 is obtained according to equation (1) above. (Twice equation (4) plus equation (1) equals equation (3)). It can further be seen that both N,N'-diaryl urea and arylamine are, in net, consumed in the process to make urethane. Example 11 of U.S. Pat. No. 4,304,922 illustrates that when $RhCl_3$ is used as catalyst in combination with iron oxychloride as co-catalyst, nitrobenzene and N,N'-diphenylurea (1:2 molar ratio) are both consumed (100% and 99% conversion, respectively) to give urethane product 99% selectivity based on nitrobenzene plus N,N'-diphenylurea).

Again, like U.S. Pat. No. 4,297,501 there is no teaching of the advantage of adding a tertiary amine to the disclosed process.

Japan Kokai No. 55-7227 discloses a process in which molecular hydrogen is added, to a process for carbonylating nitroaromatic, in the presence of a palladium catalyst, to increase the reaction rate. The description of the invention specifies a palladium catalyst, accompanied by promoters such as tertiary amines, iron and vanadium compounds, and chlorine ions. All illustrated examples use a supported palladium-selenium on carbon catalyst promoted with pyridine and either $FeCl_2$ or $VOCl_3$ (these are redox-active metal chlorides). The patent teaches that the addition of hydrogen causes hydrogenation of a fraction of the nitroaromatic to generate the corresponding primary arylamine in situ. The process is thus generically similar to that of U.S. Pat. No. 4,178,455, discussed above, which illustrates by example the addition of primary arylamine to a reaction with a supported palladium catalyst promoted with $FeCl_3$. Thus, it may be concluded that primary amine generated from hydrogen will in net be consumed in the reaction to make urethane. Indeed, Japan Kokai No. 55-7227 teaches that any primary amine remaining at the end of a reaction can be returned to another reaction with more nitroaromatic, in which case the primary amine is easily converted to urethane.

In U.S. Pat. No. 4,474,978 a process is disclosed for converting a nitroaromatic to a urethane in the presence of a primary amine and a catalyst system based on palladium complexed with Group VA-chelate ligands, including bis-tertiary amino-containing ligands. The patent teaches that the redox active metal chloride and related co-catalysts are no longer needed when the above ligands are used. But, this patent does not suggest the use of rhodium in combination with said ligands and also teaches that the primary amine and/or urea are co-converted with the nitroaromatic to urethane. Thus, the process, in net, consumes added amine or urea. See the examples disclosed in the patent.

Thus, it is clear that, in the processes cited above, as the primary amine and/or urea compound is converted, in net, to urethane, its concentration decreases and its effects on reaction rate and selectivity must also decrease. Eventually, as nitroaromatic continues to be converted, either in a batch process or in a continuous process (with recycle of the remaining amine), the primary amine will be consumed to a low concentration. In order to maintain the improved rates and selectivities, which are obtained by the original addition of primary amine, urea, hydrogen, etc., it is necessary to provide additional primary amine, urea, hydrogen, etc. as the primary amine is consumed.

A few references teach the use of rhodium catalysts, in the absence of a redox-active metal co-catalysts, for the carbonylation of nitrogen-containing organic compounds to urethanes. However, these references do not teach the initial addition of primary amines, ureas, hydrogen, etc. to obtain improved activity. For example, U.S. Pat. No. 3,338,956 discloses a metal carbonyl catalyst of Group VIA, VIIA, or VIIIA for this reaction. The only such catalyst exemplified, however, is rhodium chlorocarbonyl and the rates of reaction are relatively slow. Moreover, this reference does not teach the advantages of adding a tertiary amine to the disclosed carbonylation process.

U.S. Pat. No. 3,993,685 teaches the addition of tertiary amines, especially pyridine, to platinum group metal catalysts to obtain improved activity in the absence of redox-active metal co-catalysts. Rhodium chloride and hydridocarbonyltris(triphenylphosphine) rhodium in combination with pyridine are exemplified. In this reference it is clearly pointed out that a high concentration or excess of the tertiary amine is desirable, the tertiary amine serving as both catalyst and solvent. (Note that the suggested tertiary amines are not bis(tertiary amines)).

U.S. Pat. No. 4,052,437 discloses the use of rhodium oxide as catalyst, preferentially in nitrilic solvent. $Rh_6(CO)_{16}$ as a catalyst is also exemplified in this patent. There is no suggestion that the initial addition of a primary aryl amine to the process disclosed in this patent would improve the rate. Also, there is no suggestion of the advantage of adding a tertiary amine to the catalyst disclosed therein.

An article in the Journal of Organic Chemistry 37, 2791 (1972) describes a reaction in which nitro-benzene in the presence of ethanol is carbonylated in low yield (<10%) to urethane with a catalyst comprising $Rh_6(CO)_{16}$ in pyridine solvent. The major product was aniline. Again, like U.S. Pat. No. 3,993,685, above, the pyridine is used in high concentration or excess to enable its function as a solvent for the reaction.

None of the above cited art, which discloses the use of rhodium catalysts (in the absence of redox-active metal co-catalysts) for the carbonylation of nitro-organics to urethanes, discloses the initial addition of primary amine, urea, hydrogen, etc. Moreover, the effect of initially adding primary amine to such catalysts is not predictable. Finally, the result obtained by adding a primary amine to a rhodium catalyst system essentially free from redox-active metal components, is substantially different from the result obtained when a primary amine is added to either Group VIII metal catalysts (including rhodium and palladium) in the presence of redox active metal co-catalysts or certain palladium catalysts in the absence of redox active metal co-catalysts.

There are references, which disclose the conversion of nitroaromatic to urethane in the presence of a platinum metal catalysts and in which the primary amine is not in net consumed. See copending patent applications Ser. Nos. 532,784; 532,785 and 707,885, filed Sept. 16, 1983, Sept. 16, 1983 and Mar. 4, 1985, respectively. All three applications were filed in the names of Grate, Hamm, and Valentine and all are entitled "Process for the Preparation of Urethanes". Also, see patent application Ser. No. 744,951, filed June 17, 1985, in the names of Grate and Hamm, and entitled "Process for the Preparation of Urethanes."

It is an object of this invention to provide a process for the conversion of nitro-aromatic to urethane in good rate and selectivity, without requiring continual addition of primary amine, urea, hydrogen, etc. to maintain the rate and selectivity.

It is a further object of this invention to effectively carry out the above process in the absence of redox-active metal halide co-catalysts.

It is also an object of this invention to effectively carry out the above process in the absence of a large molar excess of tertiary amine as compared to the catalyst.

SUMMARY OF THE INVENTION

It has now been surprisingly found that, in a process for carbonylating nitrogen-containing organic compounds to urethanes, in the presence of a rhodium catalyst, a substantial improvement in the rate and selectivity of the reaction may be obtained by providing a poly amino ligand having at least two tertiary amino groups capable of coordinating with rhodium. Moreover, when a primary amine is added to the reactant solution to further improve rate and selectivity, the primary amine is not in net consumed during the reaction. Thus, in a batch process, the effects of the added primary amine do not diminish as the reaction proceeds. In a continuous process, the primary amine can be constantly recycled and no further addition of primary amine, urea, hydrogen, etc. is needed to maintain the desired rate and selectivities.

While not wishing to be bound by theory, it appears that, in the rhodium catalyzed carbonylation of the above nitrogen-containing organic compound to the corresponding urethane, in the absence of a redox-active metal halide co-catalyst, the urethane is produced by oxidative carbonylation of the corresponding primary amine. This oxidative carbonylation also provides hydrogen atom equivalents for the reduction of the nitrogen-containing organic compound to the primary amine. These reactions which are illustrated below (wherein [H] represents the rhodium hydrogen carrier) must be effectively coupled to provide the desired selectivity to the urethane.

an indefinite amount of nitrogen-containing organic compound.

The primary amine can be provided directly or by the in situ alcoholysis of a urea, biuret, or allophanate compound. Urea is alcoholyzed to form amine and urethane:

$$RNHCONHR + R'OH \rightarrow RNH_2 + RNHCO_2R'$$

Biurets and allophanates similarly provide primary amine by alcoholysis under the reaction conditions.

In a carbonylation reaction wherein no primary amine, urea, biuret, or allophanate is present, initially, a fraction of the nitrogen-containing compound (e.g. nitrobenzene) can be reduced to the primary amine (aniline) by added hydrogen. It has been found that the reduction of the nitrogen-containing organic compound to a primary amine in the presence of hydrogen is rapid and provided that the molar ratio of hydrogen to the nitrogen-containing organic compound is less than 1, the remainder of the nitrogen-containing organic compound is converted to urethane by the desired reaction stoichiometry. The primary amine may also be provided in situ by the addition of water, in which case a fraction of the nitrogen-containing compound is reduced to primary amine by hydrogen equivalents obtained from shifting water and carbon monoxide to carbon dioxide.

In the initial absence of primary amine, hydrogen or water, the hydrogen equivalents required to initially reduce nitrogen-containing organic compound to the primary amine are derived by dehydrogenation of the alcohol. (In the scheme illustrated below R represents a hydrogen or hydrocarbyl radical.)

Alcohol Dehydrogenation: $R_2CHOH \longrightarrow R_2C=O + 2[H]$
Reduction/Hydrogenation: $C_6H_5NO_2 + 2CO + 2[H] \longrightarrow C_6H_5NH_2 + 2CO_2$
Net Reaction: $\overline{C_6H_5NO_2 + 2CO + R_2CHOCH \longrightarrow C_6H_5NH_2 + 2CO_2 + R_2C=O}$

DECTAILED DESCRIPTION OF THE INVENTION

The nitrogen-containing organic compound useful in the process of this invention will contain at least one non-cyclic group in which a nitrogen atom is directly attached to a single carbon atom and through a double Oxidative carbonylation: $C_6H_5NH_2 + CO + CH_3OH \longrightarrow C_6H_5NHCO_2CH_3 + 2[H]$
Reduction/hydrogenation: $C_6H_5NO_2 + 2CO + 2[H] \longrightarrow C_6H_5NH_2 + 2CO_2$
Net Reaction: $\overline{C_6H_5NO_2 + 3CO + CH_3OH \longrightarrow C_6H_5NHCO_2CH_3 + 2CO_2}$ Thus, the primary amine (illustrated by aniline) is an intermedite in the formation of urethane from the nitrogen-containing organic compound, but is not in net produced or consumed by the desired net reaction.

It has been found that the rate and selectivity of reaction, obtained with rhodium catalysts comprising a polyamino ligand having at least two tertiary amino groups capable of coordinating with rhodium in the absence of redox-active metal halide co-catalyst, are improved when the primary amine is initially present in the reaction. It has been further found that the primary amine is not in net consumed and the desired reaction stoichiometry is obtained even when primary amine is initially added to the reaction. The initial amount of primary amine and its favorable effects on the rate and selectivity of reaction persist for the conversion of bond to oxygen or another nitrogen atom. The nitrogen-containing organic compound is selected from the group consisting of nitro, nitroso, azo and azoxy compounds.

Examples of suitable nitrogen-containing organic compounds for use in the process of this invention are compounds represented by the general formulae:

$$R_1(NO_x)_y \qquad \qquad I$$

and $$R_1-RN=N(O)_z-R_2 \qquad \qquad II$$

wherein $R_1$ and $R_2$ are radicals independently selected from the group consisting of $C_1$ to $C_{20}$ hydrocarbyl radicals and substituted derivatives thereof, x is an integer of from 1 to 2, y is an integer of from 1 to 3, and z is an integer of from 0 to 1. The substituted hydrocarbyl radical may include hetereo atoms selected from the group consisting of halogen, oxygen, sulfur, nitrogen and phosphorus atoms.

The nitrogen-containing compounds represented by formula I include nitro compounds (wherein x is 2) and nitroso compounds (wherein x is 1). Suitable nitro compounds are mononitro compounds such as nitrobenzene, alkyl and alkoxy nitrobenzenes wherein the alkyl group contains up to 10 carbon atoms, aryl and aryloxy nitrobenzenes, wherein the aryl group is phenyl, toyl, naphthyl, xylyl, chlorophenyl, chloronitrobenzenes, aminonitrobenzenes, carboalkoxyamino nitrobenzenes wherein the alkoxy group has up to 10 carbon atoms, aryl and aryloxy dinitrobenzenes, trinitro compounds such as trinitrobenzene, alkyl and alkoxytrinitrobenzenes, aryl and aryloxytrinitrobenzenes, the substituents being any of those already mentioned and chlorotrinitrobenzenes as well as similarly substituted mono and polynitro derivatives of the naphthalene, diphenyl, diphenylmethane, anthracene and phenanthrene series. Substituted or unsubstituted aliphatic nitro compounds such as nitromethane, nitrobutane, 2,2'-dimethyl nitrobutane, nitrocyclopentane, 3-methylnitrobutane, nitrooctadecane, 3-nitropropene-1, phenyl nitromethane, p-bromophenyl nitromethane, p-methoxy phenyl nitromethane,dinitroethane, dinitrohexane, dinitrocyclohexane, di-(nitrocyclohexyl)-methane are also suitable. The above nitro compounds may include more than one of the above substituents (in addition to the nitro group(s) such as in nitroaminoalkylbenzenes, nitroalkylcarboalkoxyamino benzenes, etc. From this group of nitro compounds nitrobenzene, nitrotoluene, dinitrobenzene, dinitrotoluene, trinitrobenzene, trinitrotoluene, mononitronaphthalene, dinitronaphthalene, 4,4'-dinitrodiphenylmethane, nitrobutane, nitrocyclohexane, p-nitrophenylnitromethane, dinitrocyclohexane, dinitromethylcyclohexane, dinitrocyclohexylmethane, nitroaminotoluene and nitrocarboalkoxyaminotoluene are preferred and in particular aromatic nitro compounds especially 2,4- and 2,6-dinitrotoluenes, meta and para dinitrobenzenes, and 5-nitro-2-methylcarboalkoxyamino-, 2-nitro-5-methyl-carboalkoxyamino-, and 3-nitro-2-methyl-carboalkoxyamino benzenes.

Examples of suitable nitroso compounds are the aromatic nitroso compounds such as nitrosobenzene, nitrosotoluene, dinitrosobenzene, dinitrosotoluene and the aliphatic nitroso compounds such as nitrosobutane, nitrosocyclohexane and dinitrosomethylcyclohexane.

The nitrogen-containing compounds represented by Formula II include both azo compounds (wherein z is 0) and azoxy compounds (wherein z is 1). Suitable compounds represented by Formula II include azobenzene, nitroazobenzne, chloroazobenzene, alkyl or aryl substituted azobenzene, azoxybenzene, nitroazoxybenzene, chloroazoxybenzene, etc.

The hydroxy-containing organic compounds for use in the process of this invenntion include compounds represented by the general formula R$_1$(OH)$_y$
III wherein R$_1$ and y are defined above.

Hydroxy compounds suitable for use in the process of the present invention may be, for example, mono- or polyhydric alcohols containing primary, secondary or tertiary hydroxyl groups as well as mono- and polyhydric phenols. Mixtures of these hydroxy compounds may also be used. The alcohols may be aliphatic or aromatic and may bear other substituents in addition to hydroxyl groups but the substituents should (except as hereinafter described) preferably be non-reactive to carbon monoxide under the reaction conditions. Especially suitable compounds are phenol and monohydric alcohols such as methyl, ethyl, n- and sec-propyl, n-, iso, sec-and tert butyl, amyl, hexyl, lauryl, cetyl, benzyl, chlorobenzyl and methoxybenzyl alcohols as well as diols such as ethylene glycol, diethylene glycol, propylene glycol and dipropylene glycol, triols such as glycerol, trimethylyol propane, hexanetriol, tetrols such as pentaerythritol and the ethers of such polyols providing that at least one hydroxyl group remains unetherified. The etherifying group in such ether alcohols normally contains up to 10 carbon atoms and is preferably an alkyl, cycloalkyl or aralkyl group which may be substituted with, for example, a halogen or an alkyl group.

The most preferred hydroxyl-containing organic compound for use in the process of this invention is methyl alcohol or a similar lower alkanol, e.g. a C$_1$ to C$_5$ alcohol.

The process of this invention includes the use of any mixture of nitro compounds, nitroso compounds, azo or azoxy compounds with any mixture of hydroxy compounds and also the use of compounds containing both functions, i.e. hydroxynitro compounds, hydroxynitroso compounds, hydroxyazo and hydroxyazoxy compounds such as 2-hydroxynitroethane, 2-hydroxynitrosoethane, nitrophenols, nitronaphthols, nitrosophenols, nitrosonaphthols, hydroxyazobenznes and hydroxyazoxybenzenes. Mixtures of these nitrogen-containing compounds may also be used.

This process of the invention has been found to proceed most smoothly to give the highest yields when employing nitro compounds. It is accordingly preferred to use nitro compounds rather than nitroso, azo or azoxy compounds.

The catalyst utilized in the process of this invention may be selected from the group consisting of rhodium salts, e.g. the halides, nitrate, sulfate, acetate, formate, carbonate, etc. and rhodium complexes (especially rhodium carbonyl complexes) including ligands capable of coordinating with the rhodium atom. The complex may include one or more rhodium atoms and suitable ligands may include carbon-carbon unsaturated groups as in ethylene, isobutylene, cyclohexene, norbornadiene, cyclooctatetraene. Other suitable ligands include acetylacetonate (acac), hydrogen atoms, carbon monoxide, nitric oxide, alkyl-radicals, alkyl or aryl nitriles or isonitriles, nitrogen-containing heterocyclic compounds such as pyridine, piperidine, and organo phosphines, arsines or stilbines.

The rhodium catalyst further comprises a polyamino ligand having at least two tertiary amino groups capable of coordinating with rhodium. For example, such polyamino ligand may be selected from the group of compounds represented by the general formula:

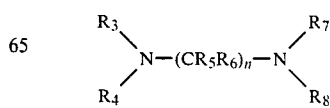

wherein $R_3$, $R_4$, $R_7$ and $R_8$, which may be the same or different, each represent an alkyl, aryl, alkaryl or aralkyl group which may be substituted by one or more inert substituents or $R_3$ and $R_4$ and/or $R_7$ and $R_8$ may form a ring structure together with the atom N to which they are attached; $R_5$ and $R_6$, which may be the same or different, each represent a hydrogen atom or a lower alkyl group and may form a ring structure together with the atom N and $R_3$, $R_4$, $R_7$ and/or $R_8$ and n is an integer, preferably n varies from 1 to about 5, e.g. 1 to 3.

Examples of ligands according to the general formula are 1,2-bis(diethylamino)ethane 1,2-bis(dimethylamino)propane, 1,2-bis(dimethylamino)ethane, 1,2-bis(di-t-butylamino)ethane, 1,2-bis(diphenylamino)ethane, 1,2-bis(diphenylamino)propane, 1,2-bis(diphenylamino)butane, 2,2'-bipyridine, 2,2'-biquinoline, bispyridylglyoxal, and 1,10-phenanthroline and derivatives thereof. Preference is given to the use of 2,2'-bipyridine and 1,10-phenanthroline.

The rhodium catalyst is preferably utilized as a homogeneous catalyst and therefore one criteria for the selection of the rhodium compound is its solubility under the conditions of reaction in the mixture of the nitrogen-containing organic compound, the hydroxyl-containing organic compound and the primary amino compound. The rhodium compound is also selected with a view toward the catalytic activity of the compound.

The rhodium compound comprising a polyamino ligand may be preformed or formed in situ in the reaction solution by separately dissolving a rhodium compound and a polyamino ligand. Since the catalyst is utilized in very low concentration, it is preferred that the compound is preformed to ensure that the polyamino ligand will be coordinated with the rhodium during the reaction.

The rhodium catalyst may be used in mixture with co-catalysts or promoters so long as the co-catalyst, unlike the redox-active metal halide co-catalysts of the prior art, does not change the reactivity of the catalyst system to consume added amines. Mono-tertiary amines are one class of suitable promoters for the rhodium catalysts of this invention. Suitable mono-tertiary amines are those described in U.S. Pat. No. 3,993,685 herein incorporated by reference.

The primary amine compound utilized in one embodiment of this invention may be selected from the group consisting of compounds represented by the general formula:

    IV wherein $R_1$ and Y are as defined above. Examples of such primary amines include methylamine, ethylamine, butylamine, hexylamine, ethylenediamine, propylenediamine, butylenediamine, cyclohexylamine, cyclohexyldiamine, aniline, p-toluidine, o-m-and p-diaminobenzenes, aminomethylcarbanilic acid esters, especially the 5-amino-2-methyl-, 2-amino-5-methyl-, and 3-amino-2-methyl carboalkoxyaminobenzenes, wherein said alkoxy group has up to 10 cabon atoms, o-, m- and p-nitroanilines, nitroaminotoluenes, especially those designated above, o-and p-phenylenediamine, benzylamine, o-amino-p-xylene, 1-aminophthaline, 2,4-and 2,6-diaminotoluenes, 4,4'-diaminodibenzyl, bis (4-aminophenyl) thioether, bis (4-aminophenyl) sulfone, 2,4,6-triaminotoluene, o-, m-and p-chloroanilines, p-bromoaniline, 1-fluoro-2,4-diaminobenzene, 2,4-diaminophenetole, o-,m- and p-aminoanisoles, ethyl p-aminobenzoate, 3-aminophthalic anhydride, etc.

These primary amino compounds may be used alone or in combination.

Among the above-enumerated primary amino compounds, those which can be derived from the starting nitro compound are preferred. For example, when nitrobenzene is used as the starting aromatic nitro compound, aniline is preferred. Similarly, 2-amino-4-nitrotoluene, 4-amino-2-nitrotoluene, and 2,4-diaminotoluene are preferably used when the starting aromatic nitro compound is 2,4-dinitrotoluene, while 2-amino-6-nitrotoluene, and 2,6-diaminotoluene are preferably used when the starting aromatic nitro compound is 2,6-dinitrotoluene.

The primary amine compound can be provided by the in-situ decomposition of the corresponding urea or biuret as represented by compounds having the general formulae:

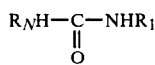

and

respectively, wherein $R_1$ is as defined above. Of course, since the above urea and biuret will comprise more than one radical, $R_1$ may represent different radicals in the same compound. That is non-symmetrical ureas and biurets, e.g.

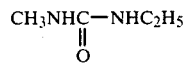

are within the scope of the invention.

In the process of this invention, no particular limitation is placed on the amount of primary amine used. However, it is preferably used in an amount equal to from 0.1 to 100 moles per gm-atom of nitrogen in the nitrogen-containing organic compound.

The process of the invention may be carried out in the absence of solvent but the use of a solvent is not precluded. Suitable solvents include, for example, aromatic solvents such as benzene, toluene, xylene, etc.; nitriles such as acetonitrile, benzonitrile, etc.; sulfones such as sulfolane, etc.; halogenated aliphatic hydrocabons such as 1,1,2-trichloro-1,,2,2,-trifluoroethane, etc.; halogenated aromatic hydrocarbons such as monochlorobenzene, dichlorobenzene, trichlorobenzene, etc.; ketones; esters; and other solvents such as tetrahydrofuran, 1,4-dioxane, 1,2-dimethoxyethane, etc.

In carrying out the process of the invention, the hydroxyl-containing organic compound and carbon monoxide may be used in amounts equal to at least 1 mole per gm-atom of nitrogen in the nitrogen-containing compound. Preferably the hydroxyl-containing organic compound is used in excess and functions as a solvent as well as a reactant.

The amount of the rhodium compound used as the catalyst may vary widely according to the type thereof and other reaction conditions. However, on a weight basis, the amount of catalyst is generally in the range of from $1 \times 10^{-5}$ to 1 part, and preferably from $1 \times 10^{-4}$ to $5 \times 10^{-1}$ parts, per gram-atom of nitrogen in the starting nitrogen-containing organic compound when expressed in terms of its metallic component.

The reaction temperature is generally held in the range of 80° to 230° C., and preferably in the range of from 100° to 200° C.

The reaction pressure, or the initial carbon monoxide pressure, is generally in the range of from 10 to 1,000 kg/cm$^2$G, and preferably from 30 to 500 kg/cm$^2$G.

The reaction time depends on the nature and amount of the nitrogen-containing organic compound used, the reaction temperature, the reaction pressure, the type and amount of catalyst used, the type of reactor employed, and the like, but is generally in the range of from 5 minutes to 6 hours. After completion of the reaction, the reaction mixture is cooled and the gas is discharged from the reactor. Then, the reaction mixture is subjected to any conventional procedure including filtration, distillation, or other suitable separation steps, whereby the resulting urethane is separated from any unreacted materials, any by-products, the solvent, the catalyst, and the like.

The urethanes prepared by the process of the invention have wide applications in the manufacture of agricultural chemicals, isocyanates, and polyurethanes.

The invention is more fully illustrated by the following examples. However, they are not to be construed to limit the scope of the invention.

In each of the following examples, the reaction was conducted in batch mode in a 300 ml stainless steel autoclave reactor equipped with a stirring mechanism which provides constant dispersion of the gas through the liquid solution. Heating of the reaction is provided by a jacket-type furnace controlled by a proportioning controller. The autoclave is equipped with a high pressure sampling system for removal of small samples of the reaction solution during the reaction in order to monitor the reaction progress. Reaction solutions were prepared and maintained under anaerobic conditions. Reaction samples were analyzed by gas chromatography.

The following examples are shown for the purpose of illustration only and should not be deemed as limiting the scope of the invention.

EXAMPLE 1

0.103 g (0.400 millimole) dicarbonylacetylacetonato rhodium and 0.072 g (0.400 millimole) 1,10-phenanthroline were mixed in methanol, giving a deep purple-black solution. 12.31 g (0.100 mole) nitrobenzene, 4.66 g (0.050 mole) aniline, 2.68 g t-butylbenzene (internal standard) and additional methanol were added to give a total solution volume of 75 ml. The solution was placed in the reactor vessel and the gas volume in the reactor was replaced with carbon monoxide at 1000 psig at ambient temperature. The reactor contents were then heated to 160° C. over 1.5 hours. On reaching 160° C., approximately 50% of the nitrobenzene was converted. After 2.0 hours at 160° C., nitrobenzene conversion was complete and the solution contained 0.080 mole methyl N-phenyl carbamate (80% selectivity based on nitrobenzene). 0.065 mole aniline, 0.006 mole N-methylene aniline, and 0.001 mole N-methylaniline (summed to 20% selectivity to additional aniline based on nitrobenzene).

EXAMPLE 2

The procedure was the same as for Example 1 with the exception that 0.078 g (0.400 milligram-atoms Rh) [Rh(CO)$_2$Cl]$_2$ was used as the rhodium source. Approximately 40% of the nitrobenzene was converted as the reactor contents were heated to 160° C. After 3.0 hours at 160° C., nitrobenzene conversion was complete and the solution contained 0.089 mole methyl N-phenyl carbamate (89% selectivity based on nitrobenzene) and 0.058 mole aniline (8% selectivity to additional aniline based on nitrobenzene).

EXAMPLE 3

The procedure was the same as for Example 1 with the exception that 0.105 g (0.400 millimole) RhCl$_3$.3H$_2$O was used as the rhodium source. After 19 hours at 160° C., the solution contained 0.085 mole nitrobenzene (15% nitrobenzene conversion), 0.015 mole methyl-N-phenyl carbamate (100% selectivity to urethane based on nitrobenzene), 0.045 mole aniline and 0.004 mole N-methylaniline.

EXAMPLE 4

The procedure is the same as for Example 1 with the exception that the rhodium-phenanthroline catalyst was prepared as follows: Methanol solutions of 0.0389 g (0.200 milligram-atoms Rh) [Rh(CO)$_2$Cl]$_2$ and 0.0514 g (0.200 millimole) Ag(CF$_3$SO$_3$) were mixed. AgCl was removed by filtration, leaving a yellow homogeneous solution. A methanol solution of 0.0360 g (0.200 millimole) 1,10-phenanthroline was then added,, giving a black suspension. Aniline, nitrobenzene, t-butylbenzene, and additional methanol were then added and the reaction was conducted according to the procedure of Example 1. After 16 hours at 160° C., nitrobenzene conversion was complete and the solution contained 0.076 mole methyl N-phenyl carbamate (76% selectivity based on nitrobenzene and 0.067 mole aniline (17% selectivity to additional aniline based on nitrobenzene).

EXAMPLE 5

The procedure was the same as for Example 1 with the exception that aniline was omitted from the initial reaction solution. As the reactor contents heated to 160° C., approximately 30% of the nitrobenzene was converted. Complete nitrobenzene conversion required 5.5 hours at 160° C. and yielded 0.068 mole methyl N-phenyl carbamate (68% selectivity), 0.022 mole aniline, 0.007 mole N-methylene aniline, and 0.001 mole (N-methylaniline (summed to 30% selectivity to aniline).

EXAMPLE 6

The procedure was the same as for Example 1 with the exception that ethanol was substituted for methanol on an equal volume basis. After 2.0 hours at 160° C., the solution contained 0.055 mole nitrobenzene (45% nitrobenzene conversion), 0.020 mole ethyl-N-phenylcarbamate (44% selectivity based on nitrobenzene), and 0.074 mole aniline (53% selectivity to additional aniline based on nitrobenzene).

What is claimed is:

1. A process for converting a nitrogen-containing organic compound, selected from the group consisting of nitro, nitroso, azo, and azoxy compounds, into the corresponding urethane, by reacting a solution, comprising said nitrogen-containing organic compound and a hydroxyl-containing organic compound, with carbon monoxide, which comprises the step of:
   (a) contacting the solution with carbon monoxide, in the presence of a rhodium catalyst comprising a polyamino ligand having at least two tertiary amino groups capable of coordinating with rhodium at conditions sufficient to convert said nitrogen-containing organic compound into the corresponding urethane, wherein said polyamino ligand is selected from the group of compounds represented by the general formula:

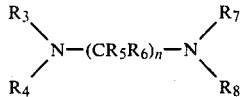

wherein $R_3$, $R_4$, $R_7$, and $R_8$, which may be the same or different, each represent an alkyl, aryl, alkaryl or aralkyl group which may be substituted by one or more inert substituents or $R_3$ and $R_4$ and/or $R_7$ and $R_8$ may form a ring stucture together with the atom N to which they are attached; $R_5$ and $R_6$, which may be the same or different, each represent a hydrogen atom or a lower alkyl group and may form a ring structure together with the atom N and $R_3$, $R_4$, $R_7$ and/or $R_8$ and n is an integer.

2. The process of claim 1 wherein said polyamino ligand is selected from the group consisting of 2,2-bipyridine and 1,10-phenanthroline.

3. The process of claim 1 wherein said nitrogen-containing organic compound is a nitro compound.

4. The process of claim 3 wherein said nitro compound is an aromatic nitro compound.

5. The process of claim 1 further comprising the step of providing a primary amine in said solution.

6. The process of claim 5 wherein said nitrogen-containing compound is an aromatic nitro compound.

7. The process of claim 6 wherein said primary amine is an aromatic amine.

8. The process of claim 7 wherein said aromatic amine corresponds to said aromatic nitro compound.

9. The process of claim 5 wherein said primary amine is provided by reducing said nitrogen-containing compound with hydrogen in said solution.

10. The process of claim 5 wherein said primary amine is provided by reducing said nitrogen-containing compound with hydrogen equivalents derived from the rhodium-catalyzed water-gas shift reaction.

11. The process of claim 5 wherein said aromatic nitro-compound is selected from the group consisting of nitrobenzene, nitroanisole, dinitrotoluene, nitromesitylene, bis(4-nitro-phenyl) methane, nitroaminotoluene and nitrocarboalkoxyaminotoluene.

12. The process of claim 7 wherein said amine is selected from the group consisting of p-toluidine, aniline, diaminotoluene, bis (4-aminophenyl) methane, aminonitrotoluene, and aminomethylcarboalkoxybenzene.

13. The processs of claim 5 wherein said amine is provided by decomposing a urea or biuret in-situ.

14. The process of claim 1 wherein said nitro-containing organic compound is converted into the corresponding urethane, by reacting said solution with carbon monoxide at a temperature of from about 100° C. to 200° C. and a carbon monoxide pressure in the range of from 30 to 500 kg/cm²G.

15. The process of claim 14 wherein said polyamino ligand is 2,2-bipyridine.

16. The process of claim 1,4 wherein said polyamino ligand is 1,10-phenanthroline.

17. The process of claim 1 wherein said rhodium catalyst is selected from the group consisting of rhodium carbonyl complexes.

18. The process of claim 7 wherein said rhodium carbonyl complex is selected from the group consisting of dicarbonyloacetylacetonato rhodium, [Rh(CO)$_2$Cl]$_2$ and Rh$_6$(CO)$_{16}$.

19. The process of claim 1 wherein said hydroxyl-containing organic compound is methanol.

20. The process of claim 1 wherein said hydroxyl-containing organic compound is ethanol.

21. The process of claim 14 wherein said hydroxyl-containing organic compound is methanol.

22. The process of claim 14 wherein said hydroxyl-containing organic compound is ethanol.

23. The process of claim 21 wherein said polyamino ligand is 1,10-phenanthroline.

24. The process of claim 1 wherein n is 2 or more.

* * * * *